(12) United States Patent
Clavel et al.

(10) Patent No.: US 8,992,953 B2
(45) Date of Patent: Mar. 31, 2015

(54) COSMETIC COMPOSITIONS HAVING VOLATILE LINEAR ALKANES

(75) Inventors: Euriel Clavel, Paris (FR); Pascal Arnaud, L'Haye-les-Roses (FR)

(73) Assignee: L'Oreal, Paris (FR)

(*) Notice: Subject to any disclaimer, the term of this patent is extended or adjusted under 35 U.S.C. 154(b) by 898 days.

(21) Appl. No.: 12/504,985

(22) Filed: Jul. 17, 2009

(65) Prior Publication Data

US 2010/0015073 A1 Jan. 21, 2010

Related U.S. Application Data

(60) Provisional application No. 61/089,576, filed on Aug. 18, 2008.

(30) Foreign Application Priority Data

Jul. 21, 2008 (FR) ...................... 08 54940

(51) Int. Cl.
- *A61K 8/31* (2006.01)
- *A61K 8/97* (2006.01)
- *A61K 8/06* (2006.01)
- *A61K 8/19* (2006.01)
- *A61Q 1/02* (2006.01)
- *A61K 8/92* (2006.01)
- *A61K 8/02* (2006.01)

(52) U.S. Cl.
CPC . *A61K 8/06* (2013.01); *A61K 8/922* (2013.01); *A61Q 1/02* (2013.01); *A61K 8/0241* (2013.01); *A61K 2800/412* (2013.01)
USPC .............. 424/401; 424/687; 424/63

(58) Field of Classification Search
None
See application file for complete search history.

(56) References Cited

U.S. PATENT DOCUMENTS

| | | | |
|---|---|---|---|
| 4,278,657 A | 7/1981 | Tezuka et al. | |
| 5,412,004 A | 5/1995 | Tachibana et al. | |
| 5,750,723 A | 5/1998 | Eldin et al. | |
| 5,811,487 A | 9/1998 | Schulz, Jr. et al. | |
| 5,847,156 A | 12/1998 | Eldin et al. | |
| 2004/0043043 A1 | 3/2004 | Schlyter et al. | |
| 2006/0292096 A1* | 12/2006 | Yu | 424/64 |
| 2008/0269352 A1* | 10/2008 | Falkowski et al. | 514/762 |

FOREIGN PATENT DOCUMENTS

| | | |
|---|---|---|
| EP | 0 542 669 A1 | 5/1993 |
| EP | 0 787 730 A1 | 8/1997 |
| EP | 0 787 731 A2 | 8/1997 |
| EP | 1 847 247 A1 | 10/2007 |
| FR | 2 459 657 | 1/1981 |
| FR | 2 792 190 A1 | 10/2000 |
| JP | A 2006-063062 | 3/2006 |
| WO | WO 93/04665 | 3/1993 |
| WO | WO 96/08537 | 3/1996 |
| WO | WO 2006/013413 A1 | 2/2006 |
| WO | WO 2006/066656 A1 | 6/2006 |
| WO | WO 2007/068371 A1 | 6/2007 |
| WO | WO2007068371 * | 6/2007 |

* cited by examiner

*Primary Examiner* — Rachael E Bredefeld
(74) *Attorney, Agent, or Firm* — Oliff PLC

(57) ABSTRACT

Cosmetic compositions in the form of an emulsion having at least one aqueous phase and at least one fatty phase, the fatty phase having at least one vegetable oil, and the composition having at least one volatile solvent of $C_9$ to $C_{15}$ volatile linear alkane(s) type and at least one calcium carbonate.

21 Claims, No Drawings

COSMETIC COMPOSITIONS HAVING VOLATILE LINEAR ALKANES

The present invention pertains to cosmetic compositions, especially those in the form of emulsions, for making up and/or caring for keratin materials, especially the skin and lips.

BACKGROUND

The present invention relates more particularly to emulsions comprising at least one vegetable oil.

Using vegetable oils in the formulation of cosmetic compositions has been known from early times. These oils are endowed with emollient and moisturizing properties and impart great softness to the skin.

Owing to their high polarity, however, vegetable oils may reduce the stability of emulsions.

Furthermore, these oils may give the compositions containing them an excessive greasy and sticky character, during and after their application, especially when present in a large amount. Moreover, they may cause a shine effect which may prove to be detrimental to the desired cosmetic properties, especially in the context of skincare or skin make-up, such as with foundations.

The aforementioned disadvantages may be even more pronounced when the cosmetic composition comprises an external fatty phase, such as, for example, water-in-oil (W/O) emulsions.

In order to overcome these disadvantages, proposals have already been made to combine these vegetable oils with volatile compounds, such as cyclic silicones or isododecane, in order to reduce their greasy and sticky character and so to promote the application of the cosmetic compositions.

This solution, however, does not always turn out to be satisfactory, especially when natural raw materials or those of natural origin are used to formulate the cosmetic compositions.

In parallel, though, the search by consumers for cosmetic products formed wholly or partly of plant constituents or constituents of plant origin is increasing.

For example, Patent Application WO 2007/068371 describes cosmetic compositions comprising alkanes of plant origin.

There is thus a need to be able to formulate cosmetic compositions, especially in the form of emulsions, comprising a vegetable oil and comprising a reduced amount, or even being devoid, of cyclic silicones or of petrochemical derivatives, such as isododecane.

There also exists a need to be able to provide cosmetic compositions, especially in the form of emulsions, comprising a vegetable oil and having satisfactory or even improved properties from the standpoints both of cosmetology and of stability.

There also exists a need to provide cosmetic compositions, especially in the form of emulsions, which are comfortable on application and especially which have little or no greasy and/or sticky character.

There also exists a need to have cosmetic compositions, especially in the form of emulsions, more particularly for caring for or making up the skin, which comprise a vegetable oil and have little or no shine effect.

Finally there also exists a need to have cosmetic compositions comprising an external fatty phase, for example W/O emulsions, which have improved cosmetic properties, especially emollient and/or moisturizing properties, and an improved stability, and also little if any greasy and/or sticky character.

The object of the present invention is to meet these needs.

BRIEF SUMMARY

Accordingly, in one of its first subjects, the invention provides a cosmetic composition in the form of an emulsion comprising at least one aqueous phase and at least one fatty phase, said fatty phase comprising at least one vegetable oil, and said composition further comprising at least one volatile linear alkane and/or one volatile solvent of $C_9$ to $C_{15}$ volatile linear alkane type and at least one calcium carbonate.

In another subject, the invention provides a cosmetic composition in the form of an emulsion comprising at least one aqueous phase and at least one fatty phase, said emulsion being a W/O emulsion, said fatty phase comprising at least one vegetable oil, and said composition further comprising at least one volatile linear alkane and/or one volatile solvent of $C_9$ to $C_{15}$ volatile linear alkane type and at least one calcium carbonate.

DETAILED DESCRIPTION

Unexpectedly the inventors have observed that the combination of at least one specific volatile linear alkane and/or one volatile solvent of $C_9$ to $C_{15}$ volatile linear alkane type, for example n-undecane, n-tridecane, or a mixture thereof, with at least one filler such as calcium carbonate, allows emulsions, in particular W/O emulsions, to be formulated that comprise at least one vegetable oil and that have satisfactory properties from the standpoints both of cosmetology and of stability.

The association of at least one volatile linear alkane and/or one volatile solvent of $C_9$ to $C_{15}$ volatile linear alkane type, or one of their mixtures, with at least one filler such as calcium carbonate, advantageously enable to stabilize W/O emulsions.

In one variant embodiment the volatile linear alkane and/or volatile solvent of $C_9$ to $C_{15}$ volatile linear alkane type is an alkane and/or solvent of plant origin.

For the purpose of the present invention, the term "linear alkane" is understood to mean a non-branched linear alkane in contrast with branched alkanes.

For the purposes of the invention a compound of plant origin is a compound obtained from a plant and subjected to one or more chemical modifications, for example by organic synthesis reaction.

For the purposes of the invention a plant compound is a compound obtained directly from a plant, without having undergone chemical modification.

Accordingly, as illustrated by the examples, the inventors have observed that it is possible to enhance the stability of an emulsion, in particular a W/O emulsion, comprising as its vegetable oil macadamia or jojoba oil, optionally in a mixture with soya oil, by introducing a mixture of n-undecane and of n-tridecane and calcium carbonate into the emulsion.

Moreover the compositions of the invention advantageously have little or no sticky and/or greasy effect on application.

Finally, the compositions of the invention exhibit a significantly reduced shine and hence do not adversely influence the cosmetic properties, and especially the aesthetic properties, of the care or make-up compositions. The cosmetic compositions of the invention especially do not exhibit a shine effect.

In another of its aspects the present invention provides for the use of at least one volatile linear alkane and/or one volatile solvent of $C_9$ to $C_{15}$ volatile linear alkane type, in combination with a calcium carbonate in an emulsion, comprising at least one vegetable oil, for imparting enhanced stability to said emulsion.

In another of its aspects the present invention provides for the use of at least one volatile linear alkane and/or one volatile solvent of $C_9$ to $C_{15}$ volatile linear alkane type, in combination with a calcium carbonate in a W/Q emulsion containing at least one vegetable oil, for imparting enhanced stability to said emulsion.

The present invention likewise provides a cosmetic process of making up and/or caring for keratin materials, comprising at least the application to said materials of at least one layer of a composition according to the invention.

In one variant embodiment a cosmetic make-up method of the invention may also be practiced on a synthetic substrate.

A composition of the invention is an emulsion possessing an aqueous or oily continuous phase. A composition of this kind may be, for example, an inverse (W/O) or direct (O/W) emulsion, or else a multiple emulsion (W/O/W or O/W/O).

In one variant embodiment an emulsion according to the invention is advantageously a W/O emulsion.

The present invention relates to cosmetic compositions which may take the form of a dermatological composition or of a care composition for keratin materials, especially the skin or lips, or else the form of a sun protection composition. In that case the composition may be a non-coloured composition optionally comprising cosmetic or dermatological actives. It may then be used as a care base for the keratin materials, especially the skin or lips.

A composition of the invention may also take the form of a coloured make-up product for keratin materials, especially for making up the skin or lips, such as a foundation, blusher, face powder or eye shadow, a skin colouring product, a concealer product, a lipstick, a lip balm, or else eyelash or eyebrow make-up such as a mascara.

According to the invention, keratin materials are the skin of the body and the mucous membranes, for example the face or the lips, and also the body hair and head hair, and especially the eyelashes.

In addition to the compounds stated above, the additional compounds or additives forming part of the formulation of the invention are preferably natural or of natural origin.

A natural compound is a compound obtained directly from the soil or the ground, or from plants or animals, by way, where appropriate, of one or more physical processes, such as, for example, grinding, refining, distilling, purifying or filtering.

A compound of natural origin is a natural compound which has undergone one or more auxiliary industrial or chemical treatments, producing modifications which are not detrimental to the essential qualities of this compound, and/or a compound comprising primarily natural constituents which have or have not undergone conversions, as indicated above.

Non-limitative examples of auxiliary industrial or chemical treatments which give rise to modifications that are not detrimental to the essential qualities of a natural compound include those authorized by monitoring organizations such as Ecocert (Standard for biological and ecological cosmetic products, January 2003) or those defined in manuals which are known in the art, such as Cosmetics and Toiletries Magazine, 2005, vol. 120, 9:10.

For the purposes of the invention a synthetic or artificial compound is a compound which does not meet the above definitions of natural compounds or compounds of natural origin.

Stability

The stability of a composition of the invention, and especially of an emulsion, may be evaluated by means of the following protocol.

A composition is prepared and then placed in a cycling oven, for example a Võtch VT4004 oven.

The composition is subjected to a set of successive cycles from −20° C. to +20° C. A set of at least 10 cycles is carried out.

Each of the cycles lasts 24 hours and comprises the following steps: 6 hours at 20° C., 6 hours of temperature reduction to −20° C., then 6 hours at a temperature of −20° C., and finally 6 hours of temperature increase to 20° C.

After each cycle, the macroscopic and microscopic appearances of the composition are evaluated.

At the end of 10 cycles, the composition must not exhibit modifications of its macroscopic appearance: it must remain smooth and homogeneous, without precipitation, phase separation or colour change.

The composition is observed under a microscope between slide and slide cover, at a magnification of X10. Its microscopic appearance must remain similar to the initial appearance.

In particular, degradation of the emulsion must not be observed (coarser emulsion base, coalescence as indicated by the presence of numerous large droplets, modification of the preparation edges, presence of crystals).

Volatile Solvents of Volatile Linear Alkanes Type

A composition of the invention comprises at least one volatile linear alkane and/or one volatile solvent of volatile linear alkane(s) type, the volatile linear alkanes being defined as follows.

For the purpose of the present invention, the expression "volatile solvent of volatile linear alkane(s) type" is understood to mean a solvent comprising a single compound of volatile linear alkane type or a mixture of compounds of volatile linear alkane type.

A volatile solvent of volatile linear alkane(s) type is essentially composed of volatile linear alkane(s) being described as follows.

The term "essentially" is understood to mean that the volatile solvent of volatile linear alkane(s) type contains at least 80% by weight, preferably at least 90% by weight and even at least 95% or even 98% by weight of volatile linear alkane(s) relative to the total weight of hydrocarbon in said solvent.

A volatile linear alkane and/or a volatile solvent of volatile linear alkane(s) type belong(s) to the composition of a liquid fatty phase of the invention, notably in the hydrocarbon oils phase, and more particularly in the hydrocarbon-based oils phase.

In one embodiment a volatile linear alkane and/or a volatile solvent of volatile linear alkane(s) type suitable for the invention may have a flash point in the range from 70 to 120° C., and more particularly from 80 to 100° C., and especially of approximately 89° C.

A volatile linear alkane and/or a volatile solvent of volatile linear alkane(s) type suitable for the invention is liquid at ambient temperature (approximately 25° C.).

In one embodiment a volatile linear alkane and/or a volatile solvent of volatile linear alkane(s) type suitable for the invention may contain at least a volatile linear alkane containing 9 to 15 carbon atoms, in particular 10 to 15 carbon atoms, and more particularly 11 to 13 carbon atoms.

A volatile linear alkane and/or volatile solvent of volatile linear alkane(s) type suitable for the invention may advantageously be of plant origin.

An alkane of this kind may be obtained, directly or in two or more steps, from a vegetable raw material such as an oil, butter, wax, etc.

Examples of alkanes suitable for the invention include the alkanes described in the Cognis Patent Application WO 2007/068371.

These alkanes are obtained from fatty alcohols, which in turn are obtained from copra oil or palm oil.

Examples of volatile solvent(s) of volatile linear alkane(s) type suitable for the invention include solvents containing at least one volatile linear alkane chosen among n-nonane (C9), n-decane (C10), n-undecane (C11), n-dodecane (C12), n-tridecane (C13), n-tetradecane (C14), n-pentadecane (C15), and mixtures thereof, and more particularly the mixture of n-undecane (C11) and n-tridecane (C13) which is sold as Cetiol UT by Cognis.

In one particular embodiment a volatile solvent of volatile linear alkane(s) type suitable for the invention may be selected from solvents containing at least one volatile linear alkane chosen among n-nonane, n-undecane, n-dodecane, n-tridecane and mixtures thereof.

More particularly a volatile linear alkane and/or volatile solvent of volatile linear alkane(s) type suitable for the invention may be employed in the form of an n-undecane/n-tridecane mixture.

In a mixture of this kind the n-undecane:n-tridecane weight ratio may preferably be 50:50 to 90:10, preferably from 60:40 to 80:20, preferably from 65:35 to 75:25.

More particularly a composition according to the invention may comprise an n-undecane:n-tridecane mixture in a weight ratio of 70:30.

In one particular embodiment a volatile hydrocarbon solvent suitable for the invention may have at 25° C. an evaporation rate of less than or equal to 0.13 mg/cm$^2$/min.

In one embodiment a volatile linear alkane and/or volatile solvent of volatile linear alkane(s) type suitable for the invention may have at 25° C. an evaporation rate in the range from 0.05 to 0.13 mg/cm$^2$/min, in particular from 0.08 to 0.12 mg/cm$^2$/min, and more particularly from 0.1 to 0.12 mg/cm$^2$/min.

The volatility of a volatile linear alkane and/or volatile solvent of volatile linear alkane(s) type in accordance with the invention may be evaluated especially by means of the protocol described in WO 06/013413, and more particularly by means of the protocol described below.

15 g of volatile linear alkane and/or volatile solvent of volatile linear alkane(s) type are placed in a crystallizing pan (diameter: 7 cm) which is placed on a balance located within a chamber of approximately 0.3 m$^3$ which is regulated in temperature (25° C.) and in hygrometry (relative humidity 50%).

The liquid is allowed to evaporate freely, without stirring, with ventilation provided by a fan (Papst-Motoren, article 8550 N, rotating at 2700 revolutions/minute) placed in a vertical position above the crystallizing pan containing the volatile hydrocarbon solvent, the blades being directed towards the crystallizing pan, at a distance of 20 cm from the base of the crystallizing pan.

At regular intervals of time, the mass of volatile linear alkane and/or volatile solvent of volatile linear alkane(s) type remaining in the crystallizing pan is measured.

The evaporation rates are expressed in mg of volatile linear alkane and/or volatile solvent of volatile linear alkane(s) type evaporated per unit surface area (cm$^2$) per unit time (minute).

The volatile linear alkane and/or volatile solvent of volatile linear alkane(s) type according to the invention has an evaporation rate of less than or equal to 0.13 mg/cm$^2$/min. This hence corresponds to an amount of evaporated solvent of less than or equal to 3.9 mg/cm$^2$ in 30 minutes.

A composition of the invention may contain from 0.5% to 90% by weight of volatile linear alkanes and/or volatile solvents of volatile linear alkane(s) type, in particular from 1% to 50% by weight, and more particularly from 5% to 40% by weight of volatile linear alkanes and/or volatile solvents of volatile linear alkane(s) type relative to the total weight of the composition.

Calcium Carbonate

A composition of the invention comprises at least one calcium carbonate. A calcium carbonate suitable for the invention may be of natural or synthetic origin.

Examples of natural calcium carbonate sources to be used in a composition of the invention include chalks, limestones, marbles, and mixtures thereof.

Mention may be made, for example, of the natural calcium carbonate sold under the tradename Omyapure 35 LM-OG by Omya.

The synthetic calcium carbonates may be obtained by a precipitation process.

Examples of synthetic calcium carbonate suitable for the invention include, for example, the calcium carbonate sold under the tradename Socal 90 A or Socal 2P by Solvay.

A calcium carbonate suitable for the invention may take the form of particles having an average size of from 0.1 to 20 μm, in particular from 0.5 to 10 μm, and more particularly from 1 to 5 μm.

A composition of the invention may contain from 0.1% to 20% by weight of calcium carbonate in particular from 0.5 to 15% of calcium carbonate and more particularly from 1% to 10% by weight of calcium carbonate relative to the total weight of the composition.

Vegetable Oils

A composition of the invention comprises at least one vegetable oil.

A vegetable oil may be extracted from a plant product either by single cold pressing (virgin oil) or by hot pressing and refining (refined oil).

The vegetable oils of the invention are oils extracted directly from plants, without being subjected to chemical modification.

Vegetable oils suitable for the invention include aloe oil, sweet almond oil, peach kernel oil, peanut oil, argan oil, avocado oil, candlenut oil, baobab oil, borage oil, broccoli oil, calendula oil, camelina oil, carrot oil, safflower oil, hemp oil, rapeseed oil, cottonseed oil, copra oil, marrow seed oil, wheat germ oil, jojoba oil, shea oil, alfalfa oil, lily oil, macadamia oil, corn oil, meadowfoam oil, St John's wort oil, millet oil, monoi oil, hazelnut oil, apricot kernel oil, nut oil, olive oil, evening primrose oil, barley oil, palm oil, passion flower oil, poppy oil, blackcurrant seed oil, kiwi seed oil, grape seed oil, pistachio oil, winter squash oil, pumpkin oil, quinoa oil, musk rose oil, sesame oil, rye oil, soya oil, sunflower oil, castor oil, and watermelon oil, and mixtures thereof.

In one embodiment a vegetable oil suitable for the invention may more particularly be selected from macadamia oil, jojoba oil, and mixtures thereof.

A composition according to the invention may contain from 0.5% to 80% by weight of vegetable oil, relative to the total weight of the composition, in particular from 1% to 50% by weight of vegetable oil, and more particularly from 2% to 25% by weight of vegetable oil, relative to the total weight of the composition.

Surfactants

A composition according to the invention comprises at least one surfactant, especially selected from amphoteric, anionic, cationic or nonionic surfactants, which are used alone or in a mixture.

The surfactants are generally present in the composition in a proportion of, for example, from 0.3% to 20% by weight, in particular from 0.5% to 15% by weight, and more particularly from 1% to 10% by weight of surfactants relative to the total weight of the composition.

It will be appreciated that the surfactant is selected to provide effective stabilization of the emulsions more particularly contemplated by the invention, i.e. those of O/W, W/O, or O/W/O type, in particular W/O type. This selection is part of the expertise of a person skilled in the art.

For the O/W emulsions, examples include nonionic surfactants, and especially esters of polyols with saturated- or unsaturated-chain fatty acids containing, for example, 8 to 24 carbon atoms and preferably 12 to 22 carbon atoms, and the alkoxylated derivatives thereof, i.e. those comprising ethylene oxide and/or propylene oxide units, such as glyceryl esters of a $C_8$-$C_{24}$ fatty acid, and their alkoxylated derivatives; polyethylene glycol esters of a $C_8$-$C_{24}$ fatty acid, and their alkoxylated derivatives; sorbitol esters of a $C_8$-$C_{24}$ fatty acid, and their alkoxylated derivatives; sugar (sucrose, glucose, alkylglucose) esters of a $C_8$-$C_{24}$ fatty acid, and their alkoxylated derivatives; fatty alcohol ethers; and sugar ethers of $C_8$-$C_{24}$ fatty alcohols, and mixtures thereof.

Glyceryl esters of a fatty acid include especially glyceryl stearate (glyceryl mono-, di- and/or tri-stearate) (CTFA name: glyceryl stearate) or glyceryl ricinoleate, and mixtures thereof.

Polyethylene glycol esters of a fatty acid include especially polyethylene glycol stearate (polyethylene glycol mono-, di- and/or tri-stearate), and more especially polyethylene glycol 50 EO monostearate (CTFA name: PEG-50 stearate), polyethylene glycol 100 HO monostearate (CTFA name: PEG-100 stearate), and mixtures thereof.

It is also possible to use mixtures of these surfactants, such as, for example, the product containing Glyceryl stearate and PEG-100 stearate that is sold under the name Arlacel 165 by Uniqema, and the product containing Glyceryl stearate (glyceryl mono-distearate) and potassium stearate that is sold under the name Tegin by Goldschmidt (CTFA name: glyceryl stearate SE).

Esters of a fatty acid with glucose or an alkylglucose include more particularly glucose palmitate, alkylglucose sesquistearates such as methylglucose sesquistearate, alkylglucose palmitates such as methylglucose or ethylglucose palmitate, fatty methylglucoside esters and more especially the methylglucoside diester of oleic acid (CTFA name: Methyl glucose dioleate); the mixed ester of methylglucoside and oleic acid/hydroxystearic acid mixture (CTFA name: Methyl glucose dioleate/hydroxystearate); the methylglucoside ester of isostearic acid (CTFA name: Methyl glucose isostearate); the methylglucoside ester of lauric acid (CTFA name: Methyl glucose laurate); the mixture of methylglucoside monoester and diester of isostearic acid (CTFA name: Methyl glucose sesqui-isostearate); the mixture of methylglucoside monoester and diester of stearic acid (CTFA name: Methyl glucose sesquistearate), and more particularly the product sold under the name Glucate SS by Amerchol, and mixtures thereof.

Ethoxylated ethers of a fatty acid with glucose or an alkylglucose include, for example, ethoxylated ethers of a fatty acid with methylglucose, and more particularly the polyethylene glycol ether of the diester of methylglucose and stearic acid containing approximately 20 moles of ethylene oxide (CTFA name: PEG-20 methyl glucose distearate), such as the product sold under name Glucam E-20 distearate by Amerchol; the polyethylene glycol ether of the mixture of methylglucose monoester and diester of stearic acid, containing approximately 20 moles of ethylene oxide (CTFA name: PEG-20 methyl glucose sesquistearate), and more particularly the product sold under the name Glucamate SSE-20 by Amerchol, and that sold under the name Grillocose PSE-20 by Goldschmidt, and mixtures thereof.

Sucrose esters include, for example, sucrose palmitostearate, sucrose stearate and sucrose monolaurate.

Fatty alcohol ethers include, for example, the polyethylene glycol ethers of a fatty alcohol that contain 8 to 30 carbon atoms, and especially 10 to 22 carbon atoms, such as the polyethylene glycol ethers with cetyl alcohol, stearyl alcohol and cetostearyl alcohol (mixture of cetyl and stearyl alcohols). Mention may be made, for example, of ethers containing 1 to 200 and preferably 2 to 100 ethylene oxide groups, such as those with CTFA names Ceteareth-20 and Ceteareth-30, and mixtures thereof.

Sugar ethers include especially alkylpolyglucosides, and, for example, decylglucoside, such as the product sold under the name Mydol 10 by Kao Chemicals, the product sold under the name Plantaren 2000 by Henkel, and the product sold under the name Oramix NS 10 by Seppic; caprylyl/capryl glucoside, such as the product sold under the name Oramix CG 110 by Seppic or under the name Lutensol GD 70 by BASF; laurylglucoside, such as the products sold under the names Plantaren 1200 N and Plantacare 1200 by Henkel; cocoglucoside, such as the product sold under the name Plantacare 818/UP by Henkel; cetostearyl glucoside, optionally in a mixture with cetostearyl alcohol, sold for example under the name Montanov 68 by Seppic, under the name Tego-Care CG90 by Goldschmidt and under the name Emulgade KE3302 by Henkel; arachidyl glucoside, for example in the form of the mixture of arachidic and behenic alcohols and arachidyl glucoside that is sold under the name Montanov 202 by Seppic; cocoylethylglucoside, in the form for example of the mixture (35/65) with cetyl and stearyl alcohols that is sold under name Montanov 82 by Seppic, and mixtures thereof.

For the W/O emulsions, hydrocarbon or silicone surfactants may be used.

In one variant embodiment, preference is given to hydrocarbon surfactants.

Examples of hydrocarbon surfactants include polyol polyesters such as PEG-30 dipolyhydroxystearate, sold as Arlacel P® 135 by Uniqema, and polyglyceryl-2 dipolyhydroxystearate, sold as Dehymuls PGPH by Cognis.

Examples of silicone surfactants include alkyldimethicone copolyols such as Laurylmethicone copolyol, sold under the name Dow Corning 5200 Formulation Aid by Dow Corning, and Cetyl dimethicone copolyol, sold under the name Abil EM 90 by Goldschmidt, or the polyglyceryl-4 isostearate/cetyl dimethicone copolyol/hexyl laurate mixture sold under the name Abil WE 09 by Goldschmidt.

To this system it is possible as well to add one or more co-emulsifiers. Advantageously the co-emulsifier may be selected from the group comprising polyol alkyl esters. Polyol alkyl esters include especially esters of glycerol and/or of sorbitan, and, for example, the polyglyceryl-3 diisostearate sold under the name Lameform TGI by Cognis, polyglyceryl-4 isostearate, such as the product sold under the name Isolan GI34 by Goldschmidt, sorbitan isostearate, such as the product sold under the name Arlacel 987 by ICI, glycerol sorbitan isostearate, such as the product sold under the name Arlacel 986 by ICI, and mixtures thereof.

As surfactants of W/O emulsions it is also possible to use a solid crosslinked elastomeric organopolysiloxane containing at least one alkylene oxide group, such as those obtained by the procedure of Examples 3, 4 and 8 of document U.S. Pat. No. 5,412,004 and the examples of document U.S. Pat. No. 5,811,487, especially the product of Example 3 (synthesis example) of U.S. Pat. No. 5,412,004, and as sold as KSG 21 by Shin Etsu.

Surfactants suitable for obtaining a W/O emulsion include especially the polyisobutylene surfactants with an esterified succinic end group, such as those sold under the names Lubrizol 5603® and Chemcinnate 2000® by Lubrizol and Chemron respectively. Also suitable for the invention are surfactants of amphiphilic polymer type.

Amphiphilic polymers are any polymers comprising both a hydrophilic part and a hydrophobic part and having the property of forming a film which separates two liquids of different polarity, thereby allowing liquid-liquid dispersions of direct, inverse or multiple type to be stabilized. These polymers may be water-soluble or water-dispersible.

It is possible more particularly to use acrylate/$C_{10}$-$C_{30}$-alkyl acrylate copolymers such as the products sold under the names Pemulen TR1, Pemulen TR2 and Carbobol 1382 by Goodrich, or else mixtures thereof. It is also possible to use the acrylate/steareth-20 itaconate copolymers and acrylate/ceteth-20 itaconate copolymers sold under the names Structure 2001 and Structure 3001 by National Starch. Terpolymers which can be used include the methacrylic acid/methyl acrylate/behenyl alcohol dimethyl-m-isopropenyl benzyl isocyanate terpolymer ethoxylated with 40 EO units (i.e. containing 40 ethylene oxide groups), sold by Amerchol under the name Viscophobe DB 1000 NP3-NP4.

Mention may also be made of crosslinked terpolymers of methacrylic acid, ethyl acrylate and polyethylene glycol (10 EO) ether of stearyl alcohol (Steareth 10), especially those sold by Allied Colloids under the name Salcare SC 80.

Mention may also be made of anionic polymers such as, for example, polymers of isophthalic acid or sulphoisophthalic acid, and more particularly phthalate/sulphoisophthalate/glycol copolymers (for example diethylene glycol/phthalate/isophthalate/1,4-cyclohexanedimethanol copolymers) that are sold under the name Eastman AQ polymer (AQ35S, AQ38S, AQ55S, AQ48 Ultra) by Eastman Chemical.

In one embodiment a composition of the invention may advantageously contain less than 5% by weight, or even less than 3% by weight, or even less than 2% by weight, relative to the total weight of the composition, or even may be devoid of silicone surfactants.

Physiologically Acceptable Medium

In addition to the compounds indicated above, a composition according to the invention comprises a physiologically acceptable medium.

A physiologically acceptable medium is a medium which is particularly suitable for the application of a composition of the invention to keratin materials, especially the skin and lips.

The physiologically acceptable medium is generally suited to the nature of the substrate to which the composition must be applied, and also to the way in which the composition must be packaged.

Aqueous Phase

A composition of the invention may comprise water in an amount of from 5% to 80%, and more particularly from 20% to 60%, by weight relative to the total weight of the composition.

Water suitable for the invention may be, for example, a natural spring water, such as La Roche-Posay water, or a flower water.

In one embodiment a composition of the invention may further comprise at least one water-miscible organic solvent.

The water-miscible organic solvent or solvents suitable for the invention may be selected from $C_{1-8}$, and especially $C_{1-5}$, monoalcohols, especially ethanol, isopropanol, tert-butanol, n-butanol, polyols, $C_2$-$C_8$ glycols, $C_2$-$C_6$ polyhydric alcohols, such as glycerol, and mixtures thereof.

A composition of the invention may further comprise at least one salt, for example sodium chloride, magnesium chloride and magnesium sulphate.

A composition of the invention may contain from 0.1% to 1.5% in particular from 0.4% to 1.2% and more particularly from 0.5% to 1% by weight of salts, relative to the total weight of the composition.

Liquid Fatty Phase

A cosmetic composition in accordance with the present invention may comprise—further to at least one vegetable oil as indicated above—at least one liquid and/or solid fatty phase and especially at least one oil as mentioned below.

An oil is any fatty substance in liquid form at ambient temperature (20-25° C.) and at atmospheric pressure.

A composition of the invention may comprise a liquid fatty phase in an amount of from 5% to 95%, in particular from 10% to 80%, in particular from 15% to 70%, and more particularly from 20% to 65% by weight, relative to the total weight of the composition.

The oily phase suitable for the preparation of the cosmetic compositions according to the invention may comprise hydrocarbon-based oils, hydrocarbon oils, silicone, fluoro or non-fluoro oils, or mixtures thereof.

The oils may be volatile or non-volatile.

They may be of animal, plant, mineral or synthetic origin, In one variant embodiment, oils of plant origin are preferred.

For the purpose of the present invention, the term "volatile oil" is intended to mean an oil (or non-aqueous medium) capable of evaporating on contact with the skin in less than one hour, at ambient temperature and at atmospheric pressure. The volatile oil is a volatile cosmetic oil which is liquid at ambient temperature, and which especially has a non-zero vapour pressure, at ambient temperature and at atmospheric pressure, in particular having a vapour pressure ranging from 0.13 Pa to 40000 Pa ($10^{-3}$ to 300 mmHg), preferably ranging from 1.3 Pa to 13000 Pa (0.01 to 100 mmHg), and preferentially ranging from 1.3 Pa to 1300 Pa (0.01 to 10 mmHg).

For the purpose of the present invention, the term "non-volatile oil" is intended to mean an oil having a vapour pressure of less than 0.13 Pa.

For the purpose of the present invention, the term "silicone oil" is intended to mean an oil comprising at least one silicon atom, and in particular at least one Si—O group.

The term "fluoro oil" is intended to mean an oil comprising at least one fluorine atom.

The term "hydrocarbon oil" is intended to mean an oil containing mainly hydrogen and carbon atoms, and if necessary alcohol, acid, ester or ether functions.

A hydrocarbon-based oil is exclusively composed of hydrogen and carbon atoms.

The oils may optionally comprise oxygen, nitrogen, sulphur and/or phosphorus atoms, for example in the form of hydroxyl or acid radicals.

An oil may be a polymeric or non-polymeric oil. The expression "polymeric oil" is understood to mean an oil comprising at least one or being exclusively composed of molecules composed of repeating monomers, identical or different, As polymeric oil, mention may be made of polyisobutene.

Volatile Oils

Volatile oils may be selected from hydrocarbon oils having 8 to 16 carbon atoms, and especially $C_8$-$C_{16}$ branched alkanes (also called isoparaffins), such as isododecane (also called 2,2,4,4,6-pentamethylheptane), isodecane, isohexadecane, and, for example, the oils sold under the trade names of ISOPARS® or PERMETHYLS®.

As volatile oils it is also possible to use volatile silicones such as, for example, volatile linear or cyclic silicone oils, especially those having a viscosity≤8 centistokes (cSt) ($8\times10^{-6}$ m²/s), and having, especially, from 2 to 10 silicon atoms, and in particular from 2 to 7 silicon atoms, these silicones optionally comprising alkyl or alkoxy groups having from 1 to 10 carbon atoms. Volatile silicone oils which can be used in the invention include, especially, dimethicones with a viscosity of 5 and 6 cSt, octamethylcyclotetrasiloxane, decamethylcyclopentasiloxane, dodecamethylcyclo-hexasiloxane, heptamethylhexyltrisiloxane, heptamethyloctyltrisiloxane, hexamethyl-disiloxane, octamethyltrisiloxane, decamethyltetrasiloxane, dodecamethylpentasiloxane, and mixtures thereof.

It is also possible to use volatile fluoro oils, such as nonafluoromethoxybutane or perfluoromethylcyclopentane, and mixtures thereof.

Non-Volatile Oils

The non-volatile oils may in particular be selected from non-volatile hydrocarbon, fluoro and/or silicone oils.

As non-volatile hydrocarbon oil, mention may in particular be made of:

hydrocarbon oils of animal origin, hydrocarbon oils of plant origin, such as phytostearyl esters, for instance phytostearyl oleate, phytostearyl isostearate and lauroyl/octyldodecyl/phytostearyl glutamate (Ajinomoto, Eldew PS203), triglycerides composed of fatty acid esters of glycerol, in particular in which the fatty acids may have chain lengths ranging from $C_4$ to $C_{36}$, and in particular from $C_{18}$ to $C_{36}$, it being possible for these oils to be linear or branched, and saturated or unsaturated; these oils may in particular be heptanoic or octanoic triglycerides, or alternatively caprylic/capric acid triglycerides, for instance those sold by STEARINERIES DUBOIS or those sold under the names MIGLYOL 810®, 812® and 818® by DYNAMIT NOBEL, synthetic ethers containing from 10 to 40 carbon atoms, such as dicapryl ether;

synthetic esters, for instance oils of formula $R_1COOR_2$, in which $R_1$ represents a linear or branched fatty acid residue containing from 1 to 40 carbon atoms and $R_2$ represents a hydrocarbon chain, in particular a branched chain, containing from 1 to 40 carbon atoms provided that $R_1+R_2$ is ≥10. The esters may in particular be selected from esters of an alcohol fatty acid, such as, for example:

cetostearyl octanoate, isopropyl alcohol esters, such as isopropyl myristate or isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic esters, for instance isodecyl neopentanoate and isotridecyl neopentanoate, and isononanoic esters, for instance isononyl isononanoate and isotridecyl isononanoate, polyol esters and pentaerythritol esters, for instance dipentaerythritol tetrahydroxy-stearate/tetraisostearate, fatty alcohols that are liquid at ambient temperature, with a branched and/or unsaturated carbon chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid or linolenic acid, and mixtures thereof and dialkyl carbonates, the 2 alkyl chains possibly being identical or different, such as dicaprylyl carbonate sold under the name CETIOL CC® by COGNIS, oils of high molar mass, having in particular a molar mass ranging from approximately 400 to approximately 2000 g/mol, in particular from approximately 650 to approximately 1600 g/mol. As oils of high molar mass that can be used in the present invention, mention may in particular be made of the oils selected from:

a) esters, such as:

esters of linear fatty acids having a total carbon number ranging from 35 to 70, such as pentaerythrityl tetrapelargonate, hydroxylated esters, such as polyglyceryl-2 triisostearate, aromatic esters, such as tridecyl trimellitate, esters of $C_{24}$-$C_{28}$ branched fatty acids or fatty alcohols, such as those described in U.S. Pat. No. 6,491,927, and pentaerythritol esters, and especially triisoarachidyl citrate, glyceryl triisostearate, glyceryl 2-tridecyl tetradecanoate, polyglyceryl-2 tetraisostearate or else pentaerythrityl 2-tetradecyl tetradecanoate, b) silicone oils, such as phenyl silicones, for instance Belsil PDM 1000 from the company Wacker (MM=9000 g/mol). Other non-volatile silicone oils that can be used in the composition according to the invention may be non-volatile polydimethylsiloxanes (PDMS), PDMS comprising alkyl or alkoxy groups that are pendant and/or at the end of a silicone chain, these groups each containing 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyltrimethicones with a viscosity of less than or equal to 100 cSt, and mixtures thereof, and also mixtures of these various oils, In one embodiment a composition of the invention may advantageously contain less than 10% by weight, or even less than 5% by weight, or even less than 2% by weight relative to the total weight of the composition, or may even be devoid, of silicone oil, more particularly of cyclic silicone oil, and/or of mineral oil, and/or of branched volatile alkanes not directly obtained from plants or not of plant origin, such as isododecane or isoparaffins.

In another embodiment, a composition of the invention may contain at least 20% by weight of volatile linear alkane and/or volatile solvent of volatile linear alkane(s) type relative to the total weight of hydrocarbon oil of the composition.

In one embodiment a composition of the invention may contain at least 30%, or even at least 40%, in particular at least 50%, notably at least 60%, more particularly at least 70% and more particularly at least 80%, at least 90% or 100% of volatile linear alkane and/or volatile solvent of volatile linear alkane(s) type relative to the total weight of hydrocarbon oil of the composition.

A composition according to the invention containing 100% of volatile linear alkane and/or volatile solvent of volatile linear alkane(s) type relative to the total weight of hydrocarbon oil comprise a hydrocarbon oil phase composed exclusively of volatile linear alkane and/or volatile solvent of volatile linear alkane(s) type.

In one variant embodiment, a composition according to the invention may contain at least 20% of volatile linear alkane and/or volatile solvent of volatile linear alkane(s) type relative to the total weight of hydrocarbon-based oil, in particular relative to the total weight of saturated hydrocarbon-based oil, and preferably relative to the total weight of non-polymeric saturated hydrocarbon-based oil of the composition.

In one embodiment a composition of the invention may contain at least 30%, or even at least 40%, in particular at least 50%, notably at least 60%, more particularly at least 70%, and more particularly at least 80%, at least 90% or 100% of volatile linear alkane and/or volatile solvent of volatile linear alkane(s) type relative to the total weight of hydrocarbon-based oil, in particular relative to the total weight of saturated hydrocarbon-based oil, and preferably relative to the total weight of non-polymeric saturated hydrocarbon-based oil of the composition.

In one variant embodiment, a hydrocarbon-based oil considered in the previous embodiments may present a molar mass below 650 g/mol, and in particular below 400 g/mol.

A composition of the invention containing 100% of volatile linear alkane and/or volatile solvent of volatile linear alkane(s) type relative to the total weight of hydrocarbon-based oil or of saturated hydrocarbon-based oil, or of non-polymeric saturated hydrocarbon-based oil, comprise a hydrocarbon-based oil, saturated hydrocarbon-based oil or of non-polymeric saturated hydrocarbon-based oil phase exclusively composed of volatile linear alkane and/or volatile solvent of volatile linear alkane(s) type.

Lipophilic Structuring Agent

A composition according to the invention may comprise at least one agent for structuring a liquid fatty phase, selected from a wax and a pasty compound and mixtures thereof.

A composition according to the invention may comprise an amount of agent for structuring a liquid fatty phase of from 0.1% to 20% by weight, relative to the total weight of the composition, and in particular from 0.3% to 15% of agent for structuring a liquid fatty phase, and more particularly from 0.5% to 10% by weight of an agent for structuring a liquid fatty phase, relative to the total weight of the composition.

Wax(es)

A composition of the invention may comprise at least one wax.

A wax suitable for the invention is, in general, a lipophilic compound which is solid at ambient temperature (25° C.) and which has a melting point of greater than or equal to 30° C., possibly ranging up to 200° C., and especially up to 120° C.

On bringing a wax to the liquid state (melting), it is possible to render it miscible with oils and to form a macroscopically homogeneous mixture, but, on bringing the temperature of the mixture back to ambient temperature, recrystallization of the wax in the oils of the mixture is obtained.

A wax suitable for the invention may have a melting point of greater than or equal to 45° C., and in particular greater than or equal to 55° C.

For the purpose of the invention, the melting point corresponds to the temperature of the most endothermic peak observed by thermal analysis (DSC) as described in ISO standard 11357-3; 1999. The melting point of the wax can be measured using a differential scanning calorimeter (DSC), for example the calorimeter sold under the name "MDSC 2920" by the company TA Instruments.

A wax that can be used in a composition of the invention may be selected from waxes that are solid at ambient temperature.

In particular, a wax suitable for the invention may be selected from waxes of animal, plant, mineral or synthetic origin, and mixtures thereof.

In one variant embodiment, waxes of plant origin are preferred.

By way of illustration of waxes suitable for the invention, mention may in particular be made of hydrocarbon waxes, such as beeswax, lanolin wax and Chinese insect waxes; rice bran wax, carnauba wax, candelilla wax, ouricury wax, esparto wax, berry wax, shellac wax, Japan wax and sumac wax; montan wax, orange and lemon waxes, microcrystalline waxes, paraffins and ozokerite; polyethylene waxes, waxes obtained by Fischer-Tropsch synthesis and waxy copolymers, and esters thereof.

Mention may also be made of $C_{20}$-$C_{60}$ microcrystalline waxes, such as Microwax HW.

Mention may also be made of the MW 500 polyethylene wax sold as Permalen 50-L polyethylene.

Mention may also be made of waxes obtained by catalytic hydrogenation of animal or plant oils having linear or branched $C_8$-$C_{32}$ fatty chains.

Among these, mention may in particular be made of isomerized jojoba oil, such as the transisomerized partially hydrogenated jojoba oil manufactured or sold by the company Desert Whale under the commercial reference Iso-Jojoba-50®, hydrogenated sunflower oil, hydrogenated castor oil, hydrogenated copra oil, hydrogenated lanolin oil and di(1,1,1-trimethylolpropane) tetrastearate sold under the name Hest 2T-4S® by the company Heterene.

Mention may also be made of silicone waxes ($C_{30-45}$ alkyl dimethicone) and fluorinated waxes.

Use may also be made of the waxes obtained by hydrogenation of castor oil esterified with cetyl alcohol, which are sold under the names Phytowax ricin 16L64® and 22L73® by the company Sophim. Such waxes are described in application FR-A-2792190.

As wax, use may be made of a $C_{20}$-$C_{40}$ alkyl(hydroxystearyloxy)stearate (the alkyl group containing from 20 to 40 carbon atoms), alone or as a mixture.

Such a wax is in particular sold under the names Kester Wax K 82 P®, Hydroxypolyester K 82 P® and Kester Wax K 80 P® by the company Koster Keunen.

In one embodiment a composition of the invention may advantageously contain less than 10% by weight, relative to the total weight of the composition, of silicone waxes and/or of mineral waxes, or even less than 5% by weight, or even less than 2% by weight of silicone waxes and/or mineral waxes, relative to the total weight of the composition, or may even be devoid of silicone waxes and/or mineral waxes.

Pasty Compounds

A composition according to the invention may comprise at least one pasty compound. The presence of a pasty compound may make it possible advantageously to confer improved comfort when a composition of the invention is applied to keratin materials.

Such a compound may advantageously be selected from:
lanolin and derivatives thereof
polymeric or non-polymeric silicone compounds,
polymeric or non-polymeric fluorinated compounds,
vinyl polymers, in particular:
    olefin homopolymers,
    olefin copolymers,
    hydrogenated diene homopolymers and copolymers, linear or branched and homo- or copolymeric oligomers of alkyl (meth)acrylates preferably having a $C_8$-$C_{30}$ alkyl group, homo- and copolymeric oligomers of vinyl esters having $C_8$-$C_{30}$ alkyl groups, homo- and copolymeric oligomers of vinyl ethers having $C_8$-$C_{30}$ alkyl groups, fat-soluble polyethers resulting from polyetherification between one or more $C_2$-$C_{100}$, more particularly $C_2$-$C_{50}$, diols, fatty acid or alcohol esters, and mixtures thereof.

Among the esters, mention may in particular be made of:

the esters of an oligomeric glycerol, especially the esters of diglycerol, in particular the condensates of adipic acid and of glycerol, for which a portion of the hydroxyl groups of the glycerols have reacted with a mixture of fatty acids, such as stearic acid, capric acid, stearic acid and isostearic acid and 12-hydroxystearic acid, such as in particular those sold under the Softisan 649 brand by the company Sasol, or such as bis-diglyceryl polyacyladipate-2, the arachidyl propionate sold under the Waxenol 801 brand by Alzo, phytosterol esters, triglycerides of fatty acids and derivatives thereof, such as hydrogenated cocoglycerides, noncrosslinked polyesters resulting from the polycondensation between a linear or branched $C_4$-$C_{50}$ dicarboxylic acid or polycarboxylic acid and a $C_2$-$C_{50}$ diol or polyol, aliphatic esters of an ester resulting from the esterification of an aliphatic hydroxycarboxylic acid ester with an aliphatic carboxylic acid, and mixtures thereof.

In one embodiment, a composition of the invention may advantageously contain less than 10% by weight, relative to the total weight of the composition, of pasty silicone compounds and/or pasty fluorine compounds, or even less than 5% by weight of pasty silicone compounds and/or pasty fluorine compounds, or even less than 2% by weight, relative to the total weight of the composition, or may even be devoid of pasty silicone compounds and/or pasty fluorine compounds.

Gellants

According to the fluidity of the composition it is desired to obtain, it is possible to incorporate one or more gelling agents, or gellants, into a composition of the invention, especially gellants which are hydrophilic, i.e. soluble or dispersible in water.

Hydrophilic gellants include more particularly water-soluble or water-dispersible thickening polymers. These may especially be selected from the following: modified or unmodified carboxyvinyl polymers, such as the products sold under the names Carbopol (CTFA name: carbomer) by Goodrich; polyacrylates and polymethacrylates such as the products sold under the names Lubrajel and Norgel by GUARDIAN or under the name Hispagel by Hispano Chimica; polyacrylamides; polymers and copolymers of 2-acrylamido-2-methylpropanesulphonic acid, optionally crosslinked and/or neutralized, such as the poly(2-acrylamido-2-methylpropanesulphonic acid) sold by Clariant under the name Hostacerin AMPS (CTFA name: ammonium polyacryldimethyltauramide); crosslinked anionic copolymers of acrylamide and AMPS, taking the form of a W/O emulsion, such as those sold under the name Sepigel 305 (CTFA name: Polyacrylamide/C13-14 Isoparaffin/Laureth-7) and under the name Simulgel 600 (C.T.F.A. name: Acrylamide/Sodium acryloyldimethyltaurate copolymer/Isohexadecane/Polysorbate 80) by SEPPIC; polysaccharide biopolymers such as xanthan gum, guar gum, carob gum, acacia gum, scleroglucans, chitin derivatives and chitosan derivatives, carrageenans, gellans, alginates, celluloses such as microcrystalline cellulose, carboxymethylcellulose, hydroxymethylcellullose and hydroxypropylcellulose; and mixtures thereof.

Lipophilic gellants include, for example, modified clays such as modified magnesium silicate (Bentone Gel VS38 from Rheox), hectorite modified with distearyldimethylammonium chloride (CTFA name: Disteardimonium hectorite) sold under the name Bentone 38 CE by Rheox.

Colorants

A composition according to the invention may further comprise at least one colorant.

A cosmetic composition in accordance with the invention may advantageously incorporate at least one colorant selected from organic or inorganic colorants, especially those of pigment type or nacre type which are conventionally used in fat-soluble or water-soluble cosmetic compositions, materials having a specific optical effect, and mixtures thereof.

A composition according to the invention may advantageously further comprise at least one pigment.

By pigments are meant white or coloured, organic or inorganic particles which are insoluble in an aqueous solution and are intended for colouring and/or opacifying the resulting film.

The pigments may be present in a proportion of from 0.01 to 40% by weight, in particular from 0.1 to 20% by weight and specially from 1 to 15% by weight, relative to the total weight of the cosmetic composition.

Inorganic pigments useful in the invention include titanium, zirconium or cerium oxides, and also zinc, iron or chromium oxides, ferric blue, manganese violet, ultramarine blue and chromium hydrate.

The pigment in question may also be a pigment having a structure which may be, for example, of sericite/brown iron oxide/titanium dioxide/silica type. A pigment of this kind is sold for example as Coverleaf NS or JS by Chemicals and Catalysts and has a contrast ratio of around 30.

The colorant may also comprise a pigment having a structure which may be, for example, of the type of silica microspheres containing iron oxide. An example of a pigment having this structure is that sold by Miyoshi as PC Ball PC-LL-100 P, this pigment being composed of silica microspheres containing yellow iron oxide.

Organic pigments which can be used in the invention include carbon black, D & C pigments, lakes based on cochineal carmine, on barium, strontium, calcium or aluminium, or else the diketopyrrolopyrroles (DPP) described in documents EP-A-542669, EP-A-787730, EP-A-787731 and WO-A-96/08537, By "nacres" or "pearlescent pigments" are meant coloured particles of any shape, iridescent or non-iridescent, which are produced in particular by certain molluscs in their shell or else are synthesized, and which exhibit a colour effect by optical interference.

The nacres may be selected from pearlescent pigments, such as titanium mica coated with an iron oxide, titanium mica coated with bismuth oxychloride, titanium mica coated with chromium oxide, titanium mica coated with an organic dye, and pearlescent pigments based on bismuth oxychloride. The pearlescent pigment may also comprise mica particles superposed on whose surface there are at least two successive layers of metal oxides and/or of organic colorants.

Mention may also be made, as examples of nacres, of natural mica coated with titanium oxide, with iron oxide, with natural pigment or with bismuth oxychloride.

Among nacres available on the market mention may be made of Timica, Flamenco and Duochrome (based on mica), which are sold by Engelhard, the Timiron nacres sold by Merck, the Prestige mica-based nacres sold by Eckart, and the synthetic-mica-based Sunshine nacres sold by Sun Chemical.

The nacres may more particularly possess a yellow, pink, red, bronze, orange, brown, gold and/or copper colour or glint.

By way of illustration of nacres which can be employed in the context of the present invention, mention may be made in particular of the golden nacres sold in particular by Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by Merck under the name Bronze fine (17384) (Colorona) and Bronze (17353) (Colorona) and by Engelhard under the name Super bronze (Cloisonne); the orange nacres sold in particular by Engelhard under the name Orange 363C (Cloisonne) and Orange MCR 101 (Cosmica) and by Merck under the name Passion orange (Colorona) and Matt orange (17449) (Microna); the brown-hued nacres sold in particular by Engelhard under the name Nu-antique copper 340XB (Cloisonne) and Brown CL4509 (Chromalite); the copper-glint nacres sold in particular by Engelhard under the name Copper 340A (Timica); the red-glint nacres sold in particular by Merck under the name Sienna fine (17386) (Colorona); the yellow-glint nacres sold in particular by Engelhard under the name Yellow (4502) (Chromalite); the gold-glint red-hued nacres sold by Engelhard under the name Sunstone G012 (Gemtone); the pink nacres sold in particular by Engelhard under the name Tan opal G005(Gemtone); the gold-glint black nacres sold in particular by Engelhard under the name Nu antique bronze 240 AB (Timica), the blue nacres sold in particular by Merck under the name Matt blue (17433) (Microna), the silver-glint white nacres sold in particular by Merck under the name Xirona Silver, and the green-golden pinkish orangey nacres sold in particular by Merck under the name Indian summer (Xirona), and mixtures thereof.

The cosmetic composition according to the invention may also comprise water-soluble or fat-soluble dyes. The fat-soluble dyes are, for example, Sudan Red, DC Red 17, DC Green 6, β-carotene, Sudan Brown, DC Yellow 11, DC Violet 2, DC orange 5, and quinoline yellow. The water-soluble dyes are, for example, beetroot juice and caramel.

The cosmetic composition according to the invention may also include at least one material having a specific optical effect.

This effect is different from a simple, conventional hue effect—that is, a unified and stabilized effect of the kind produced by conventional colorants such as monochromatic pigments, for example. In the sense of the invention, "stabilized" signifies absence of an effect of variability of colour with the angle of observation or else in response to a temperature change.

For example, this material may be selected from particles having a metallic glint, goniochromatic colouring agents, diffracting pigments, thermochromic agents, optical brighteners, and also fibres, particularly of interference type. It will be appreciated that these various materials may be combined in such a way as to obtain simultaneous manifestation of two effects, or even of a new effect in accordance with the invention.

The metallic-glint particles which can be used in the invention are selected in particular from:
 particles of at least one metal and/or of at least one metal derivative,
 particles comprising a single-substance or multi-substance, organic or mineral substrate, at least partly coated with at least one metal-glint layer comprising at least one metal and/or at least one metal derivative; and mixtures of said particles.

Among the metals that can be present in said particles mention may be made, for example, of Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr and their mixtures or alloys (for example bronzes and brasses) are preferred metals.

By "metal derivatives" are meant compounds derived from metals, especially oxides, fluorides, chlorides and sulphides.

By way of illustration of these particles mention may be made of aluminium particles, such as those sold under the names Starbrite 1200 EAC® by Silberline, and Metalure® by Eckart.

Mention may also be made of metallic powders of copper or of alloy mixtures such as references 2844 sold by Radium Bronze, metal pigments such as aluminium or bronze, such as those sold under the names Rotosafe 700 from the company Eckart, the silica-sheathed aluminium particles sold under the name Visionaire Bright Silver from the company Eckart, and the metal alloy particles such as silica-sheathed bronze (copper and zinc alloy) powders sold under the name Visionaire Bright Natural Gold from the company Eckart.

The particles in question may be particles comprising a glass substrate, such as those sold by Nippon Sheet Class under the names Microglass Metashine.

The goniochromatic colouring agent may be selected, for example, from multilayer interference structures and liquid-crystal colouring agents.

Examples of symmetrical multilayer interference structures that may be used in compositions prepared in accordance with the invention are, for example, the following structures: Al/SiO$_2$/Al/SiO$_2$/Al, pigments having this structure being sold by the company Dupont de Nemours; Cr/MgF$_2$/Al/MgF$_2$/Cr, pigments having this structure being sold under the name Chromaflair by the company Flex; MoS$_2$/SiO$_2$/Al/SiO$_2$/MoS$_2$; Fe$_2$O$_3$/SiO$_2$/Al/SiO$_2$/Fe$_2$O$_3$, and Fe$_2$O$_3$/SiO$_2$/Fe$_2$O$_3$/SiO$_2$/Fe$_2$O$_3$, pigments having these structures being sold under the name Sicopearl by the company BASF; MoS$_2$/SiO$_2$/mica-oxide/SiO$_2$/MoS$_2$; Fe$_2$O$_3$/SiO$_2$/mica-oxide/SiO$_2$/Fe$_2$O$_3$; TiO$_2$/SiO$_2$/TiO$_2$ and TiO$_2$/Al$_2$O$_3$/TiO$_2$; SnO/TiO$_2$/SiO$_2$/TiO$_2$/SnO; Fe$_2$O$_3$/SiO$_2$/Fe$_2$O$_3$; SnO/mica/TiO$_2$/SiO$_2$/TiO$_2$/mica/SnO, pigments having these structures being sold under the name Xirona® by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various layers, different effects are obtained. Thus, with the Fe$_2$O$_3$/SiO$_2$/Al/SiO$_2$/Fe$_2$O$_3$ structure, the colour changes from green-golden to red-grey for SiO$_2$ layers of 320 to 350 nm; from red to golden for SiO$_2$ layers of 380 to 400 nm; from violet to green for SiO$_2$ layers of 410 to 420 nm; from copper to red for SiO$_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix, and also the products sold under the name Helicone® HC by the company Wacker.

Fillers

A composition in accordance with the invention may also comprise, in addition to the calcium carbonate, at least one filler, of organic or inorganic nature.

The term "filler" should be understood to mean colourless or white solid particles of any form, which are in a form that is insoluble and dispersed in the medium of the composition. Being inorganic or organic in nature, they make it possible to endow the composition with softness, mattness and uniformity to the make-up.

The fillers used in the compositions according to the present invention may be of lamellar, globular or spherical form, in the form of fibres or in any other form intermediate between these defined forms.

The fillers according to the invention may or may not be surface-coated, and in particular they may be surface-treated with silicones, amino acids, fluoro derivatives or any other substance that promotes the dispersion and compatibility of the filler in the composition.

For the purpose of the present invention, the terms "mineral fillers" and "inorganic fillers" are used interchangeably.

Among the mineral fillers that can be used in the compositions according to the invention, mention may be made of talc, mica, silica, trimethyl siloxysilicate, kaolin, bentone, magnesium carbonate, magnesium hydrogen carbonate, hydroxyapatite, boron nitrite, hollow silica microspheres (Silica Beads from Maprecos), glass or ceramic microcapsules, silica-based fillers such as Aerosil 200, Aerosil 300; Sunsphere H-33, Sunsphere H-51 sold by Asahi Glass; Chemicelen sold by Asahi Chemical; composites of silica and of titanium dioxide, such as the TSG series sold by Nippon Sheet Class, and mixtures thereof.

Among the organic fillers that can be used in the compositions according to the invention, mention may be made of polyamide powders (Nylon® Orgasol from Atochem), poly-b-alanine powder and polyethylene powder, polytetrafluoroethylene powders (Teflon®), lauroyllysine, starch, tetrafluoroethylene polymer powders, hollow polymer microspheres such as Expancel (Nobel Industry), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (for example, Tospearl® from Toshiba), polyurethane powders, in particular powders of crosslinked polyurethane comprising a copolymer, said copolymer comprising trimethylol hexyllactone. In particular, it may be a polymer of hexamethylene diisocyanate/trimethylol hexyllactone. Such particles are in particular commercially available, for example under the name Plastic Powder D-400® or Plastic Powder D-800® from the company Toshiki, carnauba microwaxes, such as that sold under the name Micro Care 350 by Micro Powders, synthetic wax microwaxes, such as that sold under the name MicroEase 114S® by Micro Powders, microwaxes composed of a mixture of carnauba wax and polyethylene wax, such as those sold under the names Micro Care 300® and 310® by Micro Powders, microwaxes composed of a mixture of carnauba wax and synthetic wax, such as that sold under the name Micro Care 325® by Micro Powders, polyethylene microwaxes, such as those sold under the names Micropoly 200®, 220®, 220L® and 250S® by Micro Powders, and polytetrafluoroethylene microwaxes, such as those sold under the names Microslip 519® and 519 L® by Micro Powders, and mixtures thereof.

Natural microwaxes or microwaxes of natural origin are preferred, such as carnauba microwaxes.

Actives

A composition of the invention may further comprise at least one cosmetic active and/or one dermatological active.

Non-limitative examples of cosmetic and/or dermatological actives suitable for the invention include the actives selected from the following agents:

moisturizers, desquamants, barrier function enhancers, depigmenting agents, antioxidants, dermodecontracting agents, anti-glycation agents, agents which stimulate the synthesis of dermal and/or epidermal macromolecules and/or prevent their degradation, agents which stimulate the proliferation of fibroblasts or keratinocytes and/or the differentiation of keratinocytes, agents promoting the maturation of the horny envelope, NO-synthase inhibitors, peripheral benzodiazepine receptor (PBR) antagonists, agents increasing the activity of the sebaceous gland, agents stimulating the energy metabolism of cells, tensioning agents, fat restructuring agents, slimming agents, agents promoting cutaneous microcirculation, calmatives and/or anti-irritants, sebo-regulating or anti-seborrheic agents, astringents, cicatrizing agents, anti-inflammatory agents, anti-acne agents, matting agents, soft-focus effect fillers, fluorescent agents, agents promoting the natural pinkish colouring of the skin, abrasive or exfoliating fillers, anti-microbial agents, and calmatives, anti-NO agents, free-radical scavengers or anti-pollution agents, sunscreen agents, vitamins such as tocopherol, and mixtures thereof.

The cosmetic and/or dermatological actives suitable for the invention may especially be selected from the agents mentioned in patent application EP 1 847 247.

In one embodiment a composition of the invention intended for sun protection of keratin materials, and especially the skin of the body or the lips, may comprise more particularly, as sunscreen agents, cinnamic derivatives, salicylic derivatives, camphor derivatives, triazine derivatives, benzophenone derivatives, dibenzoylmethane derivatives, β-diphenylacrylate derivatives, p-aminobenzoic acid derivatives, sunscreen polymers and sunscreen silicones, as are described, for example, in patent application WO 93/04665.

Furthermore, a composition of the invention may comprise tanning agents and/or artificial tanning agents for the skin, such as, for example, dihydroxyacetone (DHA).

It is part of the abilities of a person skilled in the art to select said active or actives and their amount as a function of the desired effect on the keratin materials, and so as not to cause any adverse effect on the cosmetic properties of the compositions of the invention.

Additives

A cosmetic composition according to the invention may comprise any additive normally used in the field under consideration, selected for example from film formers and, where appropriate, film-forming auxiliaries, gums, semi-crystalline polymers, antioxidants, essential oils, preservatives, fragrances, neutralizing agents, antiseptic agents, anti-UV protective agents, and mixtures thereof.

A person skilled in the art can adjust the nature and amount of the additives present in the compositions in accordance with the invention by means of routine operations, such that the cosmetic properties and the stability properties desired for these compositions are not thereby affected.

A composition according to the invention may in particular be in the form of a skin or lip make-up and/or care composition, in particular a lipstick or lip balm.

In one embodiment a composition of the invention may advantageously take the form of a foundation.

A composition of the invention may be obtained by means of any method of preparation known to a person skilled in the art.

The present invention will be understood more clearly by means of the following examples.

Said examples are presented only by way of illustration of the invention and should not be interpreted as limiting the scope thereof.

EXAMPLES

Examples 1-3

The three following foundation examples show the influence of the volatile linear alkanes of the invention (Example 2) and of the calcium carbonate (Example 3) on the stability of the composition.

Phase A4 is prepared separately by grinding the mixture (pigments/dicapryl ether) on a triple-roll mill, and then the phase is added with stirring using a Mortiz (1500 rpm) to the main beaker.

Finally phases A5, A6 and A7 are introduced.

Phase B, the aqueous phase, is prepared by adding the water heated at 95° C. to the glycerol. The sodium chloride and the sorbitol are incorporated. The benzyl alcohol is then introduced at a temperature below 40° C.

Emulsification takes place at ambient temperature: the aqueous phase is poured into the fatty phase, while the stirring speed is gradually increased to 4500 rpm. Stirring is maintained for 10 minutes.

Phase C is added with the stirring maintained until all of the phase has been incorporated.

Stability Measurement

The stability of the emulsion is measured using a cycling oven as indicated earlier.

More specifically, the foundation is placed in an impervious 30 ml pill box, which is subsequently placed in a Vötch VT4004 cycling oven.

The oven is programmed to carry out successive cycles of −20° C. to +20° C. One cycle lasts 24 hours and is broken down as follows: 6 hours at a temperature of 20° C., then 6 hours of temperature decrease to −20° C., then 6 hours at a temperature of −20° C., and lastly 6 hours of temperature increase to +20° C.

|   | Compounds/trade names | Ex. 1 (inventive) | Ex. 2 (comparative) | Ex. 3 (comparative) |
|---|---|---|---|---|
| A1 | Dicapryl ether sold as Cetiol OE by Cognis | 9.00 | 19.00 | 10.70 |
| A2 | Modified hectorite sold as Bentone 38 VCG by Elementis | 0.85 | 0.85 | 0.85 |
| A3 | PEG-30 dipolyhydroxy stearate sold as Arlacel P 135 by Uniqema | 5.00 | 5.00 | 5.00 |
| A4 | Dicapryl ether sold as Cetiol OE by Cognis | 4.00 | 4.00 | 4.00 |
|   | Yellow iron oxide coated with aluminium stearoylglutamate | 2.16 | 2.16 | 2.16 |
|   | Red iron oxide coated with aluminium stearoylglutamate | 0.59 | 0.59 | 0.59 |
|   | Black iron oxide coated with aluminium stearoylglutamate | 0.25 | 0.25 | 0.25 |
|   | Titanium dioxide coated with aluminium stearoylglutamate | 9.00 | 9.00 | 9.00 |
| A5 | Macadamia oil | 4.00 | 4.00 | 4.00 |
|   | Mixture of natural tocopherols with soya oil (50/50) | 0.50 | 0.50 | 0.50 |
| A6 | Undecane + tridecane sold as Cetiol UT by Cognis | 10.00 | 0 | 10.00 |
| A7 | Natural calcium carbonate sold as Omyapure 35 LM-OG by Omya | 4.00 | 4.00 | 0 |
| B | Demineralized water | 37.05 | 37.05 | 39.35 |
|   | Glycerol | 5.00 | 5.00 | 5.00 |
|   | Sodium chloride | 0.60 | 0.60 | 0.60 |
|   | Sorbitol in aqueous solution at 70%, sold as Neosorb 70/70 B by Roquette | 2.00 | 2.00 | 2.00 |
|   | Benzyl alcohol | 1.00 | 1.00 | 1.00 |
| C | Ethanol | 5.00 | 5.00 | 5.00 |
|   | TOTAL | 100% by mass | 100% by mass | 100% by mass |

Procedure

The ingredient of phase A1 is weighed out into a main beaker, which is then placed on a magnetic stirring plate, with stirring (bar magnet, 250 rpm) with heating (90° C.).

Phases A2 and A3 are added, with stirring and heating maintained until a homogeneous mixture is obtained.

Following each cycle, the macroscopic and microscopic appearances of the product are evaluated.

Results

The stability results corresponding respectively to the formulations of Examples 1, 2 and 3 are reported in Table I below:

TABLE I

|  | Ex 1 (inventive) | Ex 2 (comparative) | Ex 3 (comparative) |
| --- | --- | --- | --- |
| Stability, microscopic appearance. | Emulsion stable after 10 cycles. A few scattered droplets. | Unstable emulsion from cycle 4 on. | Unstable emulsion after 10 cycles. Beginning of coalescence. |

The results show that the emulsion according to the invention has a stability which is enhanced relative to that of the other emulsions.

Example 4

The foundation example below shows the effect of the nature of the filler and the superiority of calcium carbonate (Example 1 above) on the stability of the composition.

|  | Compounds/trade names | % by mass |
| --- | --- | --- |
| A1 | Dicapryl ether sold as Cetiol OE by Cognis | 9.00 |
| A2 | Modified hectorite sold as Bentone 38 VCG by Elementis | 0.85 |
| A3 | PEG-30 dipolyhydroxy stearate sold as Arlacel P 135 by Uniqema | 5.00 |
| A4 | Dicapryl ether sold as Cetiol OE by Cognis | 4.00 |
|  | Yellow iron oxide coated with aluminium stearoylglutamate | 2.16 |
|  | Red iron oxide coated with aluminium stearoylglutamate | 0.59 |
|  | Black iron oxide coated with aluminium stearoylglutamate | 0.25 |
|  | Titanium dioxide coated with aluminium stearoylglutamate | 9.00 |
| A5 | Macadamia oil | 4.00 |
|  | Mixture of natural tocopherols with soya oil (50/50) | 0.50 |
| A6 | Undecane + tridecane sold as Cetiol UT by Cognis | 10.00 |
| A7 | Filler | 4.00 |
| B | Demineralized water | 37.05 |
|  | Glycerol | 5.00 |
|  | Sodium chloride | 0.60 |
|  | Sorbitol in aqueous solution at 70%, sold as Neosorb 70/70 B by Roquette | 2.00 |
|  | Benzyl alcohol | 1.00 |
| C | Ethanol | 5.00 |
|  | TOTAL | 100% |

| Nature of the filler | |
| --- | --- |
| Ex 1 (invention) | Ex 4 (non-inventive) |
| Calcium carbonate (Omyapure 35 LM-OG, Omya) | Lauroyl Lysine (Amihope LL, Ajinomoto) |

Procedure

The compositions are prepared as indicated above.

Stability Measurement

The stability of the emulsions is measured using a cycling oven as described above.

Results

The stability results corresponding, respectively, to Examples 1 and 4 are reported in the table below:

|  | Ex 1 (inventive) | Ex 4 (comparative) |
| --- | --- | --- |
| Stability, microscopic appearance. | Stable emulsion after 10 cycles. A few scattered droplets. | Unstable emulsion after 3 cycles Emulsion coarse with separations. |

The results indicate that the emulsion of the invention has an enhanced stability.

Example 5

| Foundation - W/O emulsion | | |
| --- | --- | --- |
|  | Compounds/trade names | % by mass |
| A1 | Dicapryl ether sold as Cetiol OE by Cognis | 2.90 |
| A2 | Modified hectorite sold as Bentone 38 VCG by Elementis | 1.20 |
| A3 | PEG-30 Dipolyhydroxy stearate sold as Arlacel P 135 by Uniqema | 5.00 |
| A4 | Dicapryl ether sold as Cetiol OE by Cognis | 5.00 |
|  | Yellow iron oxide coated with aluminium stearoylglutamate | 2.52 |
|  | Red iron oxide coated with aluminium stearoylglutamate | 0.69 |
|  | Black iron oxide coated with aluminium stearoylglutamate | 0.29 |
|  | Titanium dioxide coated with aluminium stearoylglutamate | 10.50 |
| A5 | Macadamia oil | 4.00 |
|  | Mixture of natural tocopherols with soya oil (50/50) | 0.50 |
| A6 | Undecane + tridecane sold as Cetiol UT by Cognis | 13.00 |
| A7 | Natural calcium carbonate sold as Omyapure 35 LM-OG by Omya | 4.00 |
| B | Demineralized water | 32.80 |
|  | Glycerol | 5.00 |
|  | Sodium chloride | 0.60 |
|  | Sorbitol in aqueous solution at 70%, sold as Neosorb 70/70 B by Roquette | 2.00 |
|  | Benzyl alcohol | 1.00 |
| C | Silica sold as Sheron P1500 by CCIC | 4.00 |
| D | Ethanol | 5.00 |
|  | TOTAL | 100% |

Procedure

The ingredient of phase A1 is weighed out into a main beaker, which is then placed on a magnetic stirring plate, with stirring (bar magnet, 250 rpm) with heating (90° C.).

Phases A2 and A3 are added, with stirring and heating maintained until a homogeneous mixture is obtained.

Phase A4 is prepared separately by grinding the mixture (pigments/dicapryl ether) on a triple-roll mill, and then the phase is added with stirring using a Mortiz (1500 rpm) to the main beaker. Subsequently, phases A4, A5, A6 and, lastly, A7 are added to the constituents present.

Phase B, the aqueous phase, is prepared by adding the water heated at 95° C. to the glycerol, and the sodium chloride and the sorbitol are incorporated. The benzyl alcohol is then introduced at a temperature below 40° C.

Emulsification takes place at ambient temperature: the aqueous phase is poured into the fatty phase, while the stirring speed is gradually increased to 4500 rpm.

Stirring is maintained for 10 minutes.

Then phase C is added and, lastly, phase D; stirring is maintained until D is incorporated completely.

Example 6

Foundation - W/O emulsion

| | Compounds/trade names | % by mass |
|---|---|---|
| A1 | Dicapryl ether sold as Cetiol OE by Cognis | 2.90 |
| A2 | Modified hectorite sold as Bentone 38 VCG by Elementis | 1.20 |
| A3 | PEG-30 Dipolyhydroxy stearate sold as Arlacel P 135 by Uniqema | 5.00 |
| A4 | Dicapryl ether sold as Cetiol OE by Cognis | 5.00 |
| | Yellow iron oxide coated with aluminium stearoylglutamate | 2.52 |
| | Red iron oxide coated with aluminium stearoylglutamate | 0.69 |
| | Black iron oxide coated with aluminium stearoylglutamate | 0.29 |
| | Titanium dioxide coated with aluminium stearoylglutamate | 10.50 |
| A5 | Macadamia oil | 4.00 |
| | Mixture of natural tocopherols with soya oil (50/50) | 0.50 |
| A6 | Undecane + tridecane sold as Cetiol UT by Cognis | 13.00 |
| A7 | Synthetic calcium carbonate sold as Socal 90 A by SOLVAY | 4.00 |
| B | Demineralized water | 32.80 |
| | Glycerol | 5.00 |
| | Sodium chloride | 0.60 |
| | Sorbitol in aqueous solution at 70%, sold as Neosorb 70/70 B by Roquette | 2.00 |
| | Benzyl alcohol | 1.00 |
| C | Silica sold as Sheron P1500 by CCIC | 4.00 |
| D | Ethanol | 5.00 |
| | TOTAL | 100% |

Procedure

The composition is prepared as indicated in Example 5.

Example 7

Foundation - W/O emulsion

| | Compounds/trade names | % by mass |
|---|---|---|
| A1 | Dicapryl ether sold as Cetiol OE by Cognis | 9.90 |
| A2 | Modified hectorite sold as Bentone 38 VCG by Elementis | 1.00 |
| A3 | PEG-30 Dipolyhydroxy stearate sold as Arlacel P 135 by Uniqema | 5.00 |
| A4 | Dicapryl ether sold as Cetiol OE by Cognis | 5.00 |
| | Yellow iron oxide coated with aluminium stearoylglutamate | 2.16 |
| | Red iron oxide coated with aluminium stearoylglutamate | 0.59 |
| | Black iron oxide coated with aluminium stearoylglutamate | 0.25 |
| | Titanium dioxide coated with aluminium stearoylglutamate | 9.00 |
| A5 | Jojoba oil | 4.00 |
| | Mixture of natural tocopherols with soya oil (50/50) | 0.50 |
| A6 | Undecane + tridecane sold as Cetiol UT by Cognis | 8.00 |
| A7 | Synthetic calcium carbonate sold as Socal 90 A by Solvay | 3.00 |
| B | Demineralized water | 34.00 |
| | Glycerol | 5.00 |
| | Sodium chloride | 0.60 |
| | Sorbitol in aqueous solution at 70%, sold as Neosorb 70/70 B by Roquette | 2.00 |
| | Benzyl alcohol | 1.00 |
| C | Silica sold as Sheron P1500 by CCIC | 4.00 |
| D | Ethanol | 5.00 |
| | TOTAL | 100% |

Procedure

The composition is prepared as indicated in Example 5.

The invention claimed is:

1. A cosmetic composition in the form of a water-in-oil emulsion comprising:
   at least one aqueous phase;
   at least one fatty phase, said fatty phase comprising at least one vegetable oil;
   at least one volatile solvent of $C_{11}$ to $C_{13}$ volatile linear alkane(s) present in an amount ranging from 5% to 40% by weight relative to a total weight of the composition; and
   at least one calcium carbonate present in an amount ranging from 0.5% to 10% by weight relative to the total weight of the composition.

2. The composition according to claim 1, wherein said volatile solvent of volatile linear alkane(s) is of plant origin.

3. The composition according to claim 1, wherein said volatile solvent of volatile linear alkane(s) contains at least one volatile linear alkane selected from the group consisting of n-undecane, n-dodecane, n-tridecane, and mixtures thereof.

4. The composition according to claim 1, wherein said calcium carbonate is of natural origin.

5. The composition according to claim 1, comprising chalks, limestones, marbles and mixtures thereof as a calcium carbonate source.

6. The composition according to claim 1, wherein the calcium carbonate is in the form of particles having an average size of from 0.1 to 20 μm.

7. The composition according to claim 1, wherein said vegetable oil is selected from the group consisting of aloe oil, sweet almond oil, peach kernel oil, peanut oil, argan oil, avocado oil, candlenut oil, baobab oil, borage oil, broccoli oil, calendula oil, camelina oil, carrot oil, safflower oil, hemp oil, rapeseed oil, cottonseed oil, copra oil, marrow seed oil, wheat germ oil, jojoba oil, shea oil, alfalfa oil, lily oil, macadamia oil, corn oil, meadowfoam oil, St John's wort oil, millet oil, monoi oil, hazelnut oil, apricot kernel oil, nut oil, olive oil, evening primrose oil, barley oil, palm oil, passion flower oil, poppy oil, blackcurrant seed oil, kiwi seed oil, grape seed oil, pistachio oil, winter squash oil, pumpkin oil, quinoa oil, musk rose oil, sesame oil, rye oil, soya oil, sunflower oil, castor oil, and watermelon oil, and mixtures thereof.

8. The composition according to claim 1, containing from 0.5% to 80% by weight of the vegetable oil relative to the total weight of the composition.

9. The composition according to claim 1, comprising at least one surfactant in a proportion of 0.3% to 20% by weight of surfactants relative to the total weight of the composition.

10. The composition according to claim 1, further comprising at least one colorant.

11. The composition according to claim 1, further comprising at least one cosmetic active and/or dermatological active.

12. The composition according to claim 1, said composition being a foundation.

13. The composition according to claim 1, wherein the volatile solvent of volatile linear alkane(s) is a mixture of undecane and tridecane.

14. The composition according to claim 1, wherein the at least one vegetable oil is macadamia oil.

15. The composition according to claim 14, further comprising a mixture of natural tocopherols with soya oil.

16. The composition according to claim 1, containing 2% to 25% by weight of the vegetable oil relative to the total weight of the composition.

17. The composition according to claim 9, wherein the surfactant is selected from hydrocarbon surfactants.

18. The composition according to claim 17, wherein the hydrocarbon surfactant is selected from polyol polyesters.

19. The composition according to claim 18, wherein the polyol polyester is selected from the group consisting of dipolyhydroxystearate and polyglyceryl-2 dipolyhydroxystearate.

20. A method for imparting enhanced stability to a water-in-oil emulsion comprising:
  combining at least one volatile solvent of $C_{11}$ to $C_{13}$ volatile linear alkane(s) with at least one calcium carbonate in a water-in-oil emulsion comprising at least one vegetable oil;
  wherein said at least one volatile solvent of $C_{11}$ to $C_{13}$ volatile linear alkane(s) is present in an amount ranging from 5% to 40% by weight relative to a total weight of the emulsion; and
  said at least one calcium carbonate is present in an amount ranging from 0.5% to 10% by weight relative to the total weight of the emulsion.

21. A cosmetic method of making up and/or caring for keratin materials, comprising applying to said materials at least one layer of the composition as defined in claim 1.

* * * * *